United States Patent [19]

Turner

[11] Patent Number: 5,784,508
[45] Date of Patent: Jul. 21, 1998

[54] BALL, WIDE-ANGLE ILLUMINATOR FOR EYE SURGERY

[76] Inventor: R. Scott Turner, 620 Carpenter La., Philadelphia, Pa. 19119

[21] Appl. No.: 599,587

[22] Filed: Feb. 9, 1996

[51] Int. Cl.⁶ .............................. G02B 6/26; A61B 17/36
[52] U.S. Cl. .............................. 385/31; 385/33; 385/35; 385/38; 385/77; 385/78; 385/84; 606/4; 606/15; 606/16; 606/17
[58] Field of Search .......................... 385/31, 33, 35, 385/38, 76, 77, 78, 79, 81, 84, 139; 606/1, 2, 4, 5, 14, 15, 16, 17; 362/32

[56] References Cited

U.S. PATENT DOCUMENTS

| | | | |
|---|---|---|---|
| 4,889,399 | 12/1989 | Mariani et al. | 385/35 X |
| 4,989,943 | 2/1991 | Yoshinaga et al. | 385/35 X |
| 5,190,536 | 3/1993 | Wood et al. | 606/16 |
| 5,246,436 | 9/1993 | Rowe | 606/13 |
| 5,359,685 | 10/1994 | Waynant et al. | 385/35 |
| 5,361,316 | 11/1994 | Tanaka et al. | 385/35 |

*Primary Examiner*—Brian Healy
*Attorney, Agent, or Firm*—Charles L. Brodsky

[57] ABSTRACT

The illuminator of the invention takes relatively coherent light exiting from a fiber optic cable and spreads it in an even manner over a wide viewing area of an eye retina, and by securing a transparent ball to face the light output of the fiber optic cable with an air gap in-between, thus allowing a large light index differential between the fiber material and the light refracting material while having the second surface of the ball immersed in vitreous eye fluid.

14 Claims, 1 Drawing Sheet

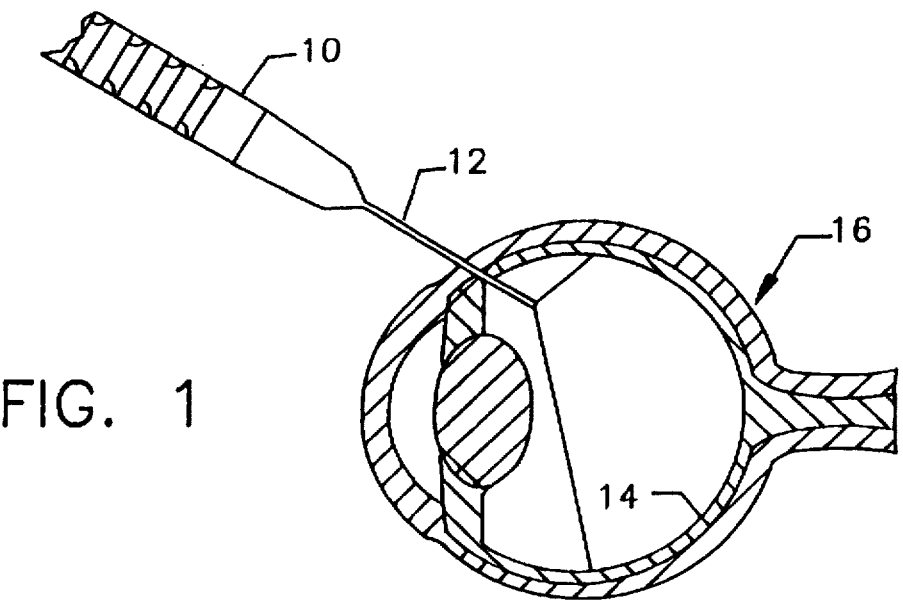
FIG. 1
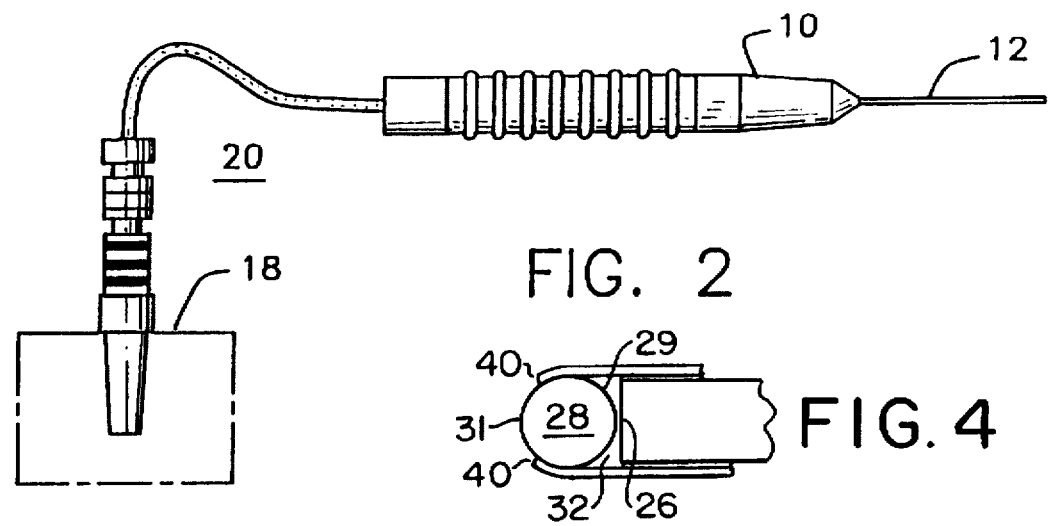
FIG. 2
FIG. 4
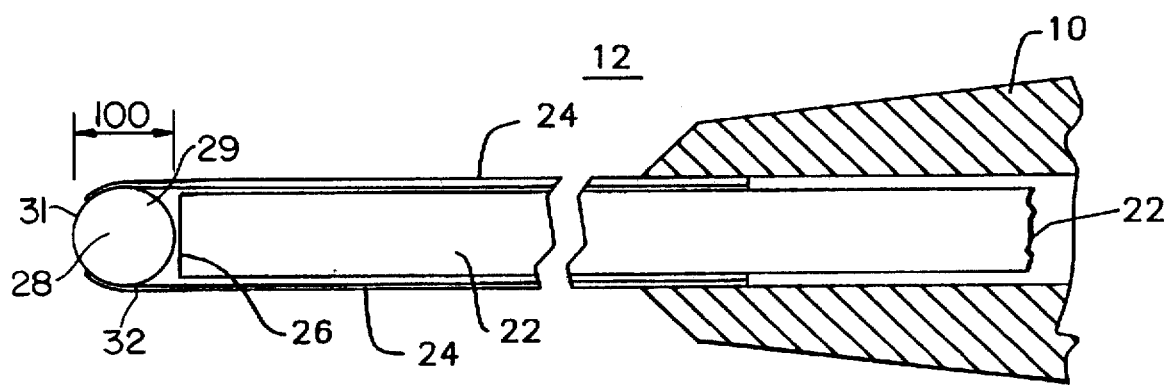
FIG. 3

BALL, WIDE-ANGLE ILLUMINATOR FOR EYE SURGERY

FIELD OF THE INVENTION

This invention relates to eye surgery, in general, and to a light-dispersing illuminator to spread the light out over the eye retina, in particular.

BACKGROUND OF THE INVENTION

As is well known and understood, in retinal eye repair surgery, it is very highly desirable for the surgeon to view as much of the retina as possible. Wide-angle viewing objective lenses have been developed by microscope manufacturers to aid in this. However, and because of back-reflected light, the illumination of the retina cannot generally be had through the same microscope lens. As a result, an opening is thus made in the eye, where a fiber optic cable is then inserted that provides a beam of light to illuminate the retinal area.

A significant problem with such an arrangement was recognized when it was realized that the largest fiber optic light beam that could be obtained on the retina was only of the order of 0.250 inches in diameter; thus attempts at increased beam-spreading the relatively coherent light was tried. Such attempts proved highly unsuccessful in practice, though, especially when placing, or forming, a lens on the end of the fiber optic cable—as analysis showed that providing any type of light refracting lens on the surface of the fiber optic cable was for the most part cancelled out, and due to the light refracting index matching of the vitreous eye fluid to that of the light refracting lens material which came in contact with such fluid. It was also found that making and aligning very small lenses was very difficult. Additional approaches to overcome this problem also prove of limited usefulness in that the light spreading that is achieved is essentially omnidirectional—i.e. spread 360°—, instead of being focused in the retinal area of concern. Additionally, and because such approaches provide a near 360° omnidirectional angle of dispersion, it was determined that a significant portion of the light being spread also is directed back through the eye lens and microscope lens through which the surgeon viewed the retina, thus producing a glare. Also, valuable light is dispersed onto areas where no viewing can be achieved.

OBJECTS OF THE INVENTION

It is an object of the present invention, therefore, to provide a new and improved wide-angle illuminator for use in retinal eye surgery.

It is another object of the invention to provide such an illuminator which is light-efficient, and which throws a minimum amount of light back into the viewing path of the microscope lens.

It is a further object of the invention to provide such a wide-angle illuminator inexpensively, and in a manner which allows the fiber optic light to be dispersed in a manner of optimum light dispersion angle.

SUMMARY OF THE INVENTION

As will become clear from the following description, the retinal illuminator of the present invention allows for the satisfaction of these objectives by taking relatively coherent light exiting from the fiber optic cable which would diverge at an angle of approximately 20° and diverge it at approximately 90° in an evenly illuminated manner over the viewing area of the retina by placing a transparent material having a light bending first surface facing the light output end of the fiber optic cable in air, thus allowing a large light index differential between the fiber material and the light dispersing material. As will be seen, in a preferred embodiment incorporating the principles of the invention, the fiber optic cable is inserted within a support tube of a handpiece stem, with the support tube extending a portion beyond the light output end of the cable; a transparent ball is secured within the extending portion of the support tube, in this embodiment, having a light bending first surface which faces the light output end of the fiber optic cable, with an air gap between such first surface and the cable's output end. To prevent the refracting index of the vitreous eye fluid from affecting the light bending which results, the apparatus of the invention will also be seen to incorporate a seal about the transparent material, between it and the inside surface of the support tube.

As will become clear from the following description, the light bending first surface of the transparent ball lens comprises this preferred embodiment of the invention, utilizing a ball lens of a material which has an index of refraction to permit the combination of first surface being in air, a second surface being in a fluid, and the curvature of the ball to refract the relatively coherent light exiting the fiber optic cable to be bent to a 90° divergence on the light exit side of the ball lens. Such ball lens may, according to the teachings of the invention, be composed of sapphire of optical grade quality.

(As is known in the prior art, ball lenses are widely used with fiber optics to broaden a very small diameter light beam and to then re-condense the light back to a very small diameter for reentering the light back into a very small diameter—as, for example, to attenuate light with a variable density neutral density light filter. Such uses will be seen quite different from using ball lenses immersed in fluids. U.S. Pat. No. 4,648,892 to Kittrel et als., on the other hand, teaches the use of lenses and other optical components at the end of fiber cables that are immersed in a vascular fluid. However, in all cases, a shield will be noted to cover the optical component to permit the desired optical effect.

U.S. Pat. No. 4,860,743 to Abela, on the other hand, teaches the use of a sapphire ball to deliver laser light to vaporize tissue in arteries. There, the ball lens is used at very close proximity to body tissue to impinge the laser light to a point; in some cases, furthermore, the ball lens is also mounted in an end cap whereby some of the light exiting the ball lens would be absorbed by the end cap to heat it.

In none of these disclosures, though, is there any suggestion of utilizing a lens of these types as a light-dispersing illuminator so as to spread the light over an eye retina in wide angle illumination.)

BRIEF DESCRIPTION OF THE DRAWING

These and other features of the present invention will be more clearly understood from a consideration of the following description, taken in connection with the accompanying drawing, in which.

FIG. 1 is a pictorial illustration of a handpiece stem inserted into the eye to illuminate the retina, helpful in an understanding of the invention;

FIG. 2 is a pictorial illustration of a cable assembly for delivering a relatively coherent light through the stem of FIG. 1

FIG. 3 is a cross-section schematic view of the stem of FIG. 1, constructed in accordance with the present invention; and FIG. 4 is a partial view of a portion of the stem of FIG. 3, helpful in understanding the teachings of the invention.

DETAILED DESCRIPTION OF THE DRAWING

In FIG. 1, a handpiece 10 typically delivers a beam of relatively coherent light through a stem 12 to illuminate the retina 14 of the eye, generally shown at 16. As will be understood, such collimated beam is generated by any appropriate light source 18 (FIG. 2) and delivered to illuminate the retina 14 by means of a coupling system 20 including a fiber optic cable which passes through the handpiece stem 12. In accordance with a preferred embodiment of the invention, the fiber optic cable used herein is selected of a diameter of the order of 0.029 inch and less, and is illustrated by the reference notation 22 in FIG. 3. Such fiber optic cable is usually encased within a support tube 24 of slightly larger inside diameter—0.030 inch for the preferred embodiment of the invention being described. As will be understood by those skilled in the art, it would be highly desirable to spread the light beam over as much of the surface of the retina 14 as the microscope wide-angle objective lens makes possible to see, yet without directing any source light back through the microscope lens being used by the eye surgeon.

Thus, and according to the invention, the support tube 24 of FIG. 3 extends a portion 100 beyond the end of the fiber optic cable, shown at 26—understood as being the "light output end" of the fiber optic cable 22. To achieve a light beam spreading, a transparent material, in the form of a ball 28, is included within the extending portion 100 of the support tube 24. More particularly, such transparent material 28 is selected to have a light bending first surface 29 facing the light output end 26 of the fiber optic cable with an air gap 32 between the two, thus allowing a large light index differential between the fiber material and the light refracting material. Such ball 28 preferably incorporates a second surface 31 being in the fluid, with the curvature of the ball 28 being such as to refract the relatively coherent light exiting the fiber optic cable to be bent to a 90° divergence on the light exit side of the ball lens 28, as at the surface 31. Such transparent ball lens material may be composed of a sapphire composition, of optical grade quality—and, in accordance with the invention, is held within the extending portion 100 of the support tube 24 by a press fit in providing a seal against vitreous eye fluids from reaching the air gap 32. To effectuate this, the ball lens 28 is fabricated of a diameter of the order of 0.001 inch larger than the inner diameter of the support tube 24—and of the order of 0.031 inch, for example, when the support tube 24 has a inside diameter of the order of 0.030 inch.

(It will also be noted that the light divergence angle can be changed by changing the ball lens material of a different index of refraction—such as optical zirconia for a larger angle or optical quartz for a smaller angle.)

As will be appreciated, by placing the transparent ball lens 28 with its light gathering and bending first surface 29 facing the light output end 26 of the fiber optic cable 22 in the air gap 32, a large light index differential is established upon the surface of the ball lens 28, and gives rise to a light bending in a manner of optimum light refraction, without the need for a large amount of light bending from the ball lens second surface while in vitreous eye fluid. To further hold the transparent ball lens 28 secured in position within the support tube 24, FIG. 4 illustrates the ends of the support tube 24 essentially being rolled-over (as at 40) about the second surface 31 of the transparent material ball lens 28, opposite to the light bending surface 29.

With the light source 18 of FIG. 2 comprising a halogen light bulb and a condensing lens, for example, the illuminator of the invention will then be effective to enable the eye surgeon to direct the light to substantially cover where he wishes in illuminating the retinal area. By specifying the dispersal angle desired, a ball lens material can be selected for the ball lens 28 either with, or without, a small degree of light "spill-over", along with its concomitant relatively small amount of light-dimming at the edges. In either event, the end result is a construction which throws a minimum amount of light back into the viewing path of the surgeon's microscope lens, and in a construction which is quite inexpensive to produce. In this manner, the relatively coherent light which exits from the fiber optic cable diverging at an angle of approximately 20° is diverged further at approximately a 90° angle in an evenly illuminated manner over the viewing area of the retina.

While there have been described what are considered to be preferred embodiments of the present invention, it will be readily appreciated by those skilled in the art that modifications can be made without departing from the scope of the teachings herein. Thus, and for example, while the wide-angle illuminator of the invention has been particularly described in context with a manner of employing it to advantage in retinal eye surgery, the teachings of the invention will apply whenever it is desired to provide light dispersal inside a body over a wide angle, as in bladder surgery. There, and generally in any type of environment where transparent fluids would interfere with obtaining a wide-angle illumination, a handpiece stem could be utilized, according to the invention, in allowing a large light index differential between the fiber material and the light dispersing material, to invasively illuminate inside a body at close proximity regardless of the relatively transparent fluid present where the handpiece stem is immersed. Additionally, and as will be understood, the teachings of the invention could apply equally as well in these or other procedures—even without the need of a handpiece—as where the wide-angle illuminator is located on the end of an endoscope, for example. For such reasons, therefore, the scope of the present invention should be read in light of the appended claims which describe the apparatus for providing this light dispersal, and the method of obtaining this type of invasive illumination, not only within the eye, but at any point within the body.

I claim:

1. In a stem to illuminate the retina of an eye, apparatus comprising:

a fiber optic cable within said stem having a light output end delivering relatively coherent light;

a support tube surrounding said fiber optic cable and extending a portion beyond said light output end;

a transparent material comprising a ball within said extended portion of said support tube;

an air gap between said light output end of said fiber optic cable and said material comprising said ball;

wherein said ball is held within said extended portion of said support tube by a seal for preventing vitreous eye fluid from reaching said air gap; and wherein said material comprising said ball is of an optical index to bend the relatively coherent light facing said ball an amount to illuminate a large portion of the retina.

2. The apparatus of claim 1 wherein said ball is held within said extended portion of said support tube by a press fit to comprise said seal.

3. The apparatus of claim 1 wherein said ball partially extends past the end of said stem.

4. The apparatus of claim 1 wherein said ball is further secured within said stem by a rolling over of the edge of said stem.

5. The apparatus of claim 1 wherein the light exiting said ball is at a divergence of approximately 90°.

6. The apparatus of claim 1 wherein said ball is composed of sapphire of optical grade quality.

7. In a handpiece stem to illuminate the retina of an eye, apparatus comprising:

> a fiber optic cable within said stem having a light output end delivering relatively coherent light;
>
> a support tube surrounding said fiber optic cable and extending a portion beyond said light output end;
>
> a transparent material comprising a ball within said extended portion of said support tube; and
>
> an air gap between said light output end of said fiber optic cable and said material comprising said ball;
>
> wherein said ball is held within said extended portion of said support tube by a press-fit to provide a seal about said ball for preventing vitreous eye fluid from reaching said air gap; and
>
> wherein said material comprising said ball is of an optical index to bend the relatively coherent light facing said ball an amount to illuminate a large portion of the retina.

8. The apparatus of claim 7 wherein said ball partially extends past the end of said handpiece stem.

9. The apparatus of claim 7 wherein said ball is further secured within said stem by a rolling over of the edge of said stem.

10. The apparatus of claim 7 wherein the light exiting said ball is at a divergence of approximately 90°.

11. The apparatus of claim 7 wherein said ball is composed of sapphire of optical grade quality.

12. A method of obtaining wide-angle illumination for retinal eye surgery by taking relatively coherent light exiting from a fiber optic cable and dispersing it in an even manner to illuminate the surface of a retina while immersed in vitreous eye fluid, by placing a transparent material comprising a ball of a curvature to refract said relatively coherent light exiting from said fiber optic cable to bend to a 90° divergence on the light exit side of said ball.

13. In a stem to provide invasive illumination inside a body over a wide angle at close proximity and in relatively transparent fluid, apparatus comprising:

> a fiber optic cable within said stem having a light output end delivering relatively coherent light;
>
> a support tube surrounding said fiber optic cable and extending a portion beyond said light output end;
>
> a transparent material comprising a ball within said extended portion of said support tube;
>
> an air gap between said light output end of said fiber optic cable and said material comprising said ball;
>
> wherein said ball is held within said extended portion of said support tube by a press-fit to provide a seal about said ball for preventing said relatively transparent fluid from reaching said air gap; and
>
> wherein said material comprising said ball is of an optical index to bend the relatively coherent light facing said ball an amount to illuminate a large portion of the retina.

14. A method of obtaining invasive illumination inside a body over a wide angle at close proximity and in a relatively transparent fluid by taking relatively coherent light exiting from a fiber optic cable and dispersing it in an even manner to illuminate the surface of a retina while immersed in vitreous eye fluid, by placing a transparent material comprising a ball of a curvature to refract said relatively coherent light exiting from said fiber optic cable to bend to a 90° divergence on the light exit side of said ball.

* * * * *